United States Patent [19]

Perlman

[11] Patent Number: 4,649,109
[45] Date of Patent: Mar. 10, 1987

[54] METHODS FOR ISOLATING MUTANT MICROORGANISMS FROM PARENTAL POPULATIONS

[75] Inventor: Daniel Perlman, Arlington, Mass.

[73] Assignee: Brandeis University, Waltham, Mass.

[21] Appl. No.: 580,854

[22] Filed: Feb. 16, 1984

[51] Int. Cl.$^4$ ................................................ C12P 1/24
[52] U.S. Cl. ...................................... 435/30; 435/182; 435/243; 435/39
[58] Field of Search .................... 435/5, 30, 32, 33, 40, 435/178, 182, 243, 261

[56] References Cited

U.S. PATENT DOCUMENTS

| 4,255,411 | 3/1981 | Lim et al. | 424/1 |
| 4,278,761 | 7/1981 | Hastings et al. | 435/178 |
| 4,352,883 | 10/1982 | Lim | 435/178 |
| 4,391,909 | 7/1983 | Lim | 435/178 |
| 4,401,755 | 8/1983 | Weaver | 435/34 |
| 4,401,762 | 8/1983 | Tellier et al. | 435/243 |
| 4,407,957 | 10/1983 | Lim | 435/178 |
| 4,409,331 | 10/1983 | Lim | 435/178 |

OTHER PUBLICATIONS

Lehinger, Biochemistry, 2nd ed., 1975, Worth Publishing, New York, pp. 157-159.

Primary Examiner—Sam Rosen
Assistant Examiner—William J. Herald
Attorney, Agent, or Firm—George W. Neuner

[57] ABSTRACT

A method for isolating a mutant microorganism is described. The method comprises the steps of: (a) separately microencapsulating in a semi-permeable membrane each or a small number of microorganisms from a microorganism population containing said mutant; (b) growing said microencapsulated microorganisms including treating to induce a detectable difference between microcapsules containing mutant microorganisms and those containing non-mutant microorganisms; and (c) separating said microcapsules containing mutant microorganisms from those containing non-mutant microorganisms based on said difference.

16 Claims, No Drawings

METHODS FOR ISOLATING MUTANT MICROORGANISMS FROM PARENTAL POPULATIONS

FIELD OF THE INVENTION

The present invention relates to a method of isolating mutant microorganisms from a population containing the same by microencapsulation techniques and to kits for practicing the methods of this invention.

BACKGROUND OF THE INVENTION

The enormous size of microbial populations has proved to be a great asset in a variety of studies, but only because it is possible to effectively select certain kinds of rare gene type or mutant microorganisms. Mutant varieties of a single strain of microorganism (procaryotic, eucaryotic or viral) have classically been isolated by a variety of methods including positive cell "selection" and differential "screening".

Selection is used to isolate mutant varieties of microorganisms when a genetic alteration provides the microorganism with a positive growth advantage over its parental population. For example, acquisition of antibiotic resistance can be used to select such mutants on a nutrient agar surface containing the antibiotic. Another example is the acquisition of a biosynthetic gene enabling the organism to grow in a culture medium that would not otherwise support growth. There are, however, other genetic alterations such as additions, substitutions or deletions of the microorganism's genome which affect the primary or secondary metabolism of the microorganism, causing a small change or negative change (decrease) in the rate of growth. Such alterations may result in a beneficial increase or decrease in the synthesis or the breakdown of chosen biochemicals. Under such circumstances, screening must generally be utilized to isolate the mutant colony. Screening may involve examination of tens of thousands of individual colonies to determine the presence of mutants. Replica plating is one such screening technique. In general, it can be said that screening techniques, although highly effective in achieving the desired result, are labor and material-intensive requiring examination of many individual colonies usually in petri dishes; replica plating and tedious visual comparison of petri dish pairs are required as well as relatively large amounts of selective and/or restrictive materials which serve to differentiate the mutant from its parent.

Recently, a technology has emerged which provides methods of encapsulating biological material such as living tissue, individual cells, viruses, and biological macromolecules within a semipermeable membrane. The basic approach in this technique involves suspending the biological material to be encapsulated in a physiologically compatible medium containing a water soluble substance that can be made insoluble in water, that is, a gel, to provide a temporary environment for the biological material. The medium is formed into droplets containing the tissue and gelled by changing any one of the variety of ambient conditions. These temporary capsules are then subjected to a treatment which results in the production of membranes with a desired permeability (including impermeable membranes). One such technique, is exemplified in U.S. Pat. No. 4,352,883 entitled "Encapsulation of Biological Material", the disclosure of which is incorporated herein by reference.

A description of a technique for separating cells having desired properties from a larger population is found in U.S. Pat. No. 4,401,755 entitled "Process for Measuring Microbiologically Active Material" which discloses a method for measuring an unknown quantity of microbiologically active material utilizing a microencapsulation techniques similar to U.S. Pat. No. 4,352,883. The disclosure of U.S. Pat. No. 4,401,755 is also incorporated herein by reference. After preparing a suspension of gel microdroplets, the suspension is processed in an apparatus having the capability of sensing a physical characteristic of individual gel microdroplets to determine the presence or absence of a desired physical characteristic of the biological material in such a droplet.

Microencapsulation technology, as described in the above referenced patents, provides the potential for solving a variety of problems including the labor and cost excesses of prior art mutant microorganism isolation techniques. It is apparent that a need to develop new isolation techniques exists which will reduce the costs and time spent in selection and screening processes used to isolate mutants from their respective parent populations.

SUMMARY OF THE INVENTION

The present invention provides a method of isolating a mutant microorganism from it's parent population in the laboratory or in a mixed multispecies population such as encountered in agricultural or industrial environment, or in fermentation. Single or small numbers of microorganisms from the parent population (containing the mutant which is desired to be isolated) are encapsulated in a semi-permeable membrane by means of microencapsulation techniques. Thereafter, the cells are cultured and the microcapsules containing substantially pure clones of microorganisms are treated to induce a detectable difference (e.g. change in number of microorganisms per microcapsule) between microcapsules containing the desired mutant microorganisms and those containing non-mutant microorganisms. This detectable difference (such as provided by a difference in cell number) serves to enable the discrimination and/or separation of microcapsules containing mutants from those with non-mutants. Finally, the microcapsules containing mutant microorganisms are isolated from those microcapsules containing non-mutant microorganisms by separation techniques based directly or indirectly on the detectable difference, e.g. a difference in microcapsule density or mass resulting from a change in cell number per microcapsule.

A non-inclusive list of characteristics which can be the basis of identifying and/or separating microencapsulated mutant cells from the parental population are increased or decreased cell growth rate, cell density, cell size, level of synthesis of a detectable primary or secondary metabolite, level of accumulation of chemical elements or compounds containing these elements, rate of breakdown of designated chemicals, antibiotic resistance and various combinations of these properties.

For instance, the difference in cell number between microcapsules containing mutant and non-mutant cells permits any one of a variety of separation techniques. These include both simultaneous (bulk or in toto) separation techniques as well as sequential (or serial) separation techniques. Examples of bulk separation include equilibrium density centrifugation, velocity or gravity sedimentation, separation in electrical or magnetic fields, chromatography, etc. Examples of serial techniques include detection of individual microcapsules via radioactive, luminescent, fluorescent or colorimetric labels, etc.

The present invention overcomes many of the prior art problems associated with isolating mutant microorganisms from parent populations in that, inter alia, it provides in some instances for separation of microcapsules containing the mutants from the microcapsules containing non-mutants without the necessity for screening techniques which involve individual examination of microorganisms and therefore can eliminate the labor and cost excesses of prior art isolation techniques. In other instances, by the increasing number of cells in microcapsules containing mutant cells a particular physical characteristic is amplified so that the mutant can more easily be separated from a parental population (where the parental population also exhibits that characteristic, but to a lessor degree).

DESCRIPTION OF THE INVENTION

In accordance with the present invention, a method is provided for isolating mutant microorganism from a parent microorganism population containing this same mutant. The method utilizes the relatively new technique of microencapsulation of biological material.

In one embodiment, the method of the present invention comprises first, microencapsulating in a semipermeable membrane individual microorganisms in the microorganism population which contains the mutant (desired to be isolated). This enables single mutant microorganisms to divide within a physical envelope so that whatever physical, chemical and/or biological identity they possess as single mutants (either a constant identity or an inducible property) can be amplified so as to facilitate the physical separation and recovery of the desired mutant.

Encapsulation of single microorganisms can be accomplished by techniques well known to those skilled in the art and, as will be appreciated, results in microcapsules which are clonally pure. In particular, single microorganism encapsulation can be readily achieved by controlling the concentration of the microorganism in suspension such that each microcapsule will receive, on average, one microorganism. Generally, the microorganisms to be encapsulated are prepared in accordance with well known prior art techniques, as individual (disaggregated) cells, and suspended in an aqueous medium suitable for maintaining viability and for supporting the ongoing metabolic processes of the particular microorganism involved. Media suitable for this purpose are available commercially. Similarly small numbers of microorganisms can be encapsulated in one microcapsule, if so desired.

The microcapsules are formed so that there is a high probability that each microcapsule contains a small number or one unit of microbiologically active material (i.e. microorganism or cell). This can be effected by regulating the dilution of the liquid composition to be used to produce the microcapsules using knowledge of the size of the microbiologically active material and the predetermined size of the microcapsule to be produced. The regulation of these factors can be determined by conventional Poisson statistical analyses so that the number of microcapsules containing more than the desired number of microbiologically active materials is more than two standard deviations from the mean. It is desirable, for example, to encapsulate zero to one microbiologically active cell per microcapsule in mutant screening and in recombination DNA research (where the object is generally to isolate desirable spontaneous mutant microorganisms or genetically engineered microorganisms from a large parental population of such microorganisms).

The preferred encapsulation technique is that described in the above-referenced U.S. Pat. No. 4,352,883 (Lim). In brief, this approach involves suspending the microorganism to be encapsulated in a physiologically compatible medium containing a water soluble substance that can be made insoluble in water (gelled) to form a temporary protective environment for the microorganisms so encapsulated. The medium is next formed into droplets containing the single microorganism and gelled, for example, by changing ambient conditions such as temperature, pH or the ionic environment. The "temporary capsules" thereby produced are then subjected to a treatment that results in the production of a membrane of a controlled permeability about the shape-retaining temporary capsules.

The temporary capsules can be fabricated from any non-toxic, water soluble substance that can be gelled to form a shape-retaining mass by a change of conditions in the medium in which it is placed, and that also comprises plural groups which are readily ionized to form anionic or cationic groups. The presence of such groups in the polymer enables surface layers of the capsule to be cross-linked to produce the desired membrane when exposed to polymers containing multiple functionalities of the opposite charge.

The presently preferred material for forming the temporary capsules is a polysaccharide gum, either natural or synthetic, of the type which can be (a) gelled to form a shape-retaining mass by being exposed to a change in conditions such as a pH change or by being exposed to multivalent cations such as $Ca^{++}$; and (b) "cross-linked" or hardened by polymers containing reactive groups such as amine or imine groups which can react with acidic polysaccharide constituents. The presently preferred gum is alkali metal alginate. Other water soluble gums which can be used include guar gum, gum arabic, carrageenan, pectin, tragacanth gum, zanthan gum or acidic fractions thereof. When encapsulating thermally refractory materials, gelatin or agar may be used in place of the gums.

The preferred method of formation of the droplets is to force the gum-nutrient-tissue suspension through a vibrating capillary tube placed within the center of the vortex created by rapidly stirring a solution containing a multivalent cation. Droplet ejected from the tip of the capillary immediately contact the solution and gel as spheriodal shaped bodies.

The preferred method of forming the desired semipermeable membrane about the temporary capsules is to "cross-link" surface layers of a gelled gum of the type having free acid groups with polymers containing acid reactive groups such as amine or imine groups. This is typically done in a dilute solution of the selected polymer. Generally, the lower the molecular weight of the polymer, the greater the penetration into the surface of the temporary capsule, and the greater the penetration, the less permeable the resulting membrane. Cross-links are produced as a consequence of salt formation between the acid reactive groups of the cross-linking polymer and the acid groups of the polysaccharide gum. Within limits, semipermeability can be controlled by selecting the molecular weight of the cross-linking polymer, its concentration, and the duration of reaction.

Cross-linking polymers which have been used with success include polyethylenimine and polylysine. Molecular weight can vary, depending on the degree of permeability required, between about 3,000 and 100,000 or more. Good results are obtained using polymers having an average molecular weight on the order of 35,000.

Optionally, with certain materials used to form the temporary capsules, it is possible to improve mass-transfer within the capsule after formation of the desired membrane by re-establishing the conditions under which the material is liquid, e.g., removing the multivalent cation. This can be done by ion exchange, e.g., immersion in phosphate buffered saline or citrate buffer. In some situations, such as where it is desired to preserve the encapsulated tissue, or where the temporary gelled capsule is permeable, it may be preferable to leave the encapsulated gum in the cross-linked, gelled state.

An alternative method of membrane formation involves an interfacial polycondensation or polyaddition reaction. This approach involves preparing a suspension of temporary capsules in an aqueous solution of the water soluble reactant which includes a pair of complementary monomers which can form a polymer. Thereafter, the aqueous phase is suspended in a hydrophobic liquid in which the complementary reactant is soluble. When the second reactant is added to the two-phase system, polymerization takes place at the interface. Permeability can be controlled by controlling the makeup of the hydrophobic solvent and the concentration of the reactants. Still another way to form a semipermeable membrane is to include a quantity of protein in the temporary capsule which can thereafter be cross-linked in surface layers by exposure to a solution of a cross-linking agent such as gluteraldehyde.

The second step of the method of the present invention preferably comprises growing the microencapsulated microorganism under conditions which induce a difference in the number of microorganisms per capsule between microcapsules containing mutant microorganisms and those containing non-mutant microorganisms. The detectable difference can be a result of the difference in cell number, per se, or the cells can be treated to amplify the difference between mutant clones and parental clones. That is, within the last three generations of growth or, in some cases, after the microorganisms within the microcapsules have been grown, they can be further treated in order to amplify particular characteristics in the material to facilitate identification and isolation of microcapsules containing mutants. Methods of treatment include incubation, incubation with heavy isotope or radioactive isotope metabolites, staining with fluorescent stains, labeling with magnetically tagged substances or immunological agents, etc.

In one embodiment of the present invention the microorganisms are grown under non-restrictive non-selective conditions within the microcapsules for several generations to a predetermined microorganism density to establish the microorganism's viability and the appropriate population number within each microcapsules. By way of example, single microorganisms are grown, using complete medium, to no more than about 5-10% of the final density within the microcapsule. At this point, it is possible, if desirable, to eliminate empty microcapsules and those containing non-viable or very slow growing organisms by for example differential density-sedimentation, because microorganisms are heavier than water. If the desired mutant is slow growing, the separation is accomplished at this point. Thereafter, the microcapsules are grown under conditions which would induce a difference in mass between mutant and non-mutant containing microcapsules. For example, restrictive and/or selective conditions could be employed during this stage of growth to induce the desired difference in cell number per capsule. If the mutant desired to be isolated, for example, is characterized in that it has acquired antibiotic resistance, then the cells within microcapsules can be cultured in a medium containing the specific antibiotic. This results in mutant growth within microcapsules while further growth of non-mutant strains in microcapsules would be prevented. If, on the other hand, the mutant requires a particular amino acid to grow, restrictive conditions can be used which will result in mutant-containing microcapsules possessing fewer microorganisms than non-mutant-containing microcapsules, hence providing the desired cell number differentiation.

This has obvious industrial importance. In isolating mutants of yeasts, molds, single cell bacteria, and actinomycetes, in which the mutants overproduce valuable enzymes and primary metabolites, it has been noted that growth of such mutants is usually slower than the parental cells. This is because unbalanced metabolism, if not producing cell toxicity, results in energy waste and nutrient limitations. These mutants, which are normally hidden in the population, can be selected in accord with the present invention by, for example, a microcapsule density centrifugation protocol. Moreover, the growth rate difference and resulting difference in cell number (which is the basis for the separation) between microcapsules containing mutant and non-mutant microorganisms may be accentuated further by a chosen feeding regimen. Depending on the metabolic process desired to be de-regulated in the mutant, an appropriate nutrient source (i.e., carbon, nitrogen, phosphate, or other essential nutrient) can be made limiting. This same growth rate selection protocol can be used to functionally differentiate mutations in genetically engineered organisms in which, out of a spectrum of mutations, very few result in enzyme or metabolite overproduction.

In another embodiment, mass differentiation between mutant and non-mutant-containing microcapsules can be enhanced by transferring the microcapsules to culture medium containing heavy isotope metabolites including, for example, deuterium oxide and/or $^{15}N$-labeled compounds for an appropriate period of time. Subsequently, the microcapsules are washed in normal culture medium such that the cells within the microcapsules selectively retain heavy isotopes. This procedure serves to increase the overall density difference between microcapsules containing many as compared to those containing few cells.

In still another embodiment, mass differentiation between mutant and non-mutant-containing microcapsules can be established by inversion of the density of the microcapsules. This is accomplished by incubating the microcapsules in any non-toxic high density medium of appropriate diffusion rate. The microcapsules containing fewer microorganisms will exchange more volume of the medium than microcapsules containing the greater number of microorganisms, thus becoming more dense and establishing the desired difference in mass.

Another distinct basis for density separation of encapsulated mutant microorganisms from the encapsulated parental microorganism population is the difference in the intrinsic density of the microorganism itself. If, for example, a mutant microorganism accumulates a heavy metal in elemental or ionic form more efficiently than the non-mutant then, after growth in the presence of such a metal, the microcapsule containing the mutants would be more dense. Similarly, other metabolites, periodic elements, or compounds thereof, which accumulate either in the microorganism or in the microcapsule and change the microcapsule density, can provide the basis of separation based on difference in mass between the various microcapsules.

The final step required in practicing the present invention comprises separating the microcapsules containing mutants from those containing non-mutants based on the detectable difference, such as the difference in number of cells per capsule therebetween. Any one of a variety of techniques well-known to those skilled in the art may be employed to effect the desired separation. In particular, where applicable, it is preferable to use equilibrium density centrifugation, or alternatively velocity sedimentation. Electrical or magnetic field separation protocols, or a combination thereof can also be used to effect separation. Automated laser cell sorting devices can similarly be utilized to sort microcapsules containing differing numbers of cells. If cells are, for example, uniformly labeled with a fluorescent dye then microcapsules containing greater numbers of cells will fluoresce with a greater intensity than microcapsules containing fewer cells. Thus, microcapsules containing mutant cells are separable from microcapsules containing non-mutant cells.

The above approach to mutant isolation is revolutionary in several senses. Once microcapsule size and porosity are chosen, the isolation of mutant microorganisms becomes a simple task. In a preferred embodiment, centrifugation replaces visual scanning of a field or any other collection of microorganism colonies. Isolation of single microcapsules containing desirable mutants is accomplished by, for instance, equilibrium density centrifugation. Once the centrifugation parameter is established for a species of microorganism, the isolation of almost any mutant of that species is facilitated.

Conditional lethal mutations can be difficult to isolate, however, because the microencapsulation method relies on non-growth, yet survival, of such mutants under restrictive growth conditions for recovery of the mutants. Many conditional lethal mutations may, however, still be isolated by the method of the present invention, because only one microorganism out of the many present in each microcapsule at the time of shift to restrictive growth conditions need survive.

Microorganisms for which the method of the present invention is useful include procaryotic cells—such as, for example, microorganisms including single cell bacteria, spores, and actinomycetes, eucaryotic cells—such as yeasts, molds and higher plant and animal cells including fused cell hybrids such as antibody-producing hybridoma cells, and virally-infected cells. A non-inclusive list of cell identities which can be the basis of identifying mutant cells are increased or decreased growth rate, cell density, cell size, level of synthesis of a detectable primary or secondary metabolite, level of accumulation of chemical elements, or compounds of these elements, rate of breakdown of designated chemicals, antibiotic resistance and various combinations of these properties.

In another embodiment, a hybridoma cell mixture (which may have been preselected for fused (hybridoma) cells with antibiotic or nutrient regimen to eliminate unfused parental cells) is suspended at a cell concentration such that each microcapsule will receive, on average, one hybridoma cell. For extremely rare monoclonal antibody selection it may be desirable to originally encapsulate a "pool" of cells, i.e., 2-50 hybridoma cells per microcapsule. Following growth and antibody expression within the microcapsules (suspended in appropriate nutrient medium) the microcapsules are screened for specific antibody production by employing a challenge antigen.

The antigen may be fluorescent or radioistope-labeled such that following incubation of the microcapsules in the presence of microcapsule-diffusible (small) antigen and thorough rinsing to remove unbound antigen, the specific binding of labeled antigen to antibody can be easily monitored. In the case of antigens larger than the effective microcapsule pore size and therefore not microcapsule-diffusible, the labeled antigen is first broken down by mechanical or enzymatic cleavage to a diffusible size and then employed in the screening.

This has enormous potential as a research tool for the following reasons. For example, if an objective is to generate monoclonal antibodies against surface determinants on a patient's cancer cells, the cancer cells or their outer membranes would be injected into a mouse to elicit antibody response. Later the individual mouse spleen cell-myeloma cell hybrids would be microencapsulated and grown to appropriate density within the microcapsules. Hybridoma cell-monoclonal antibody within these microcapsules cannot be challenged with whole cancer cells. Rather, the surface components of the intact cancer cells would be made fluorescent or radiolabeled. The cancer cells would then be broken, the labeled membrane pelleted, and this membrane then broken and/or enzymatically digested to reduce the labeled surface components to microcapsule-diffusible size. These labeled components would then be utilized for microcapsule monoclonal antibody screening. The microcapsules containing different monoclonal antibodies optionally can be pre-incubated (pre-competed) with the unlabeled (non-fluorescent and non-radioactive) cell surface components of the respective non-cancerous cells. Such pre-competing reduces the "false-positive" microcapsules, i.e. those not producing cancer-specific antibodies.

One can also differentially label (by isotope and fluorescent derivatives) different classes of macromolecules on the cancer cell surface such as protein, carbohydrate or lipid. One can then distinguish microcapsules containing antibodies directed against the different classes of cellular macromolecules.

Following the binding of labeled antigen to antibody within the microcapsule, residual unbound antigen is washed from the microcapsules using appropriate buffer or culture medium. The desired microcapsules containing radioactive and/or fluorescent bound antigen are physically separated from the gross population of microcapsules. Most easily separated are fluorescent spheres which can be harvested using an automated laser cell sorter typically employed to separate T and B lymphocyte cells. Rapid screening of radioactive (as well as fluorescent) microspheres can also be accomplished by a very different and less expensive method. First, an 8×10 inch "monolayer" of spheres can be deposited on a plate (each sphere covers approximately 0.01 mm$^2$). This layer will contain approximately 5×10$^6$ microspheres. Photographic emulsion-autoradiography can be utilized to locate the radioactive microspheres. Since these microspheres are on the order of 100 microns (0.1 mM) in diameter their autoradiographic image should be visible on film. A luminescent reference grid included in the microsphere support surface helps the investigator to align the film with the microsphere support surface and identify a small region containing the radioactive microsphere. Suction aspiration of this region yields a small number of microspheres. These small groups of microspheres are spread out and again autoradiographed to yield individual desired microspheres. For fluorescent antigen applications, the microspheres are briefly exposed during photography to UV light. Again a luminescent or fluorescent spacial reference grid is included to align the film with the microsphere support surface. The support surface between microspheres and film is preferably sufficiently thin to minimize angular dispersal of microsphere source radiation.

Current methods for selecting new and commercially important strains of microorganisms for industrial process usually involve screening single cells for altered physical or biochemical properties (under the microscope) or screening multicellular colonies derived from single cells for new biochemical properties, or for increases or decreases in existing biochemical abilities. This is particularly difficult to do when the microorganism is a member of a complex culture or ecosystem consisting of more than one species of live organism (said complex culture being also termed "non-sterile"). Furthermore, the property or properties of the desired strain (i.e. "mutant") may depend upon concerted growth of more than one microorganism in the non-sterile medium. Some examples of such non-sterile culture environments include activated-sludge process for sewage treatment, fruit and grain mash process, biomass fermentation, dairy process, petrochemical process, mineral leaching process, soil microorganism growth (nitrogen fixation, etc.), swamp and lake eutrification process, etc. In accord with the method of the present invention in order to obtain a mutant of a particular microorganism strain for industrial process, the microorganism is microencapsulated as described above. After incubating the microcapsules in the complex culture environment, the microcapsules are recovered and those containing the desired mutant cells are selected as described herein. Valuable new mutants of desired species can thus be isolated from such complex environments. One can select, screen, and recover mutant cells which have grown to microcolonies within the microcapsules while they are in "communication" via diffusion with the complex environment.

It is easy to see that state of the art isolation of plant or animal cell mutants, e.g. mammalian cells in tissue culture, is revolutionized by the method of present invention. This envisions encapsulation of single cells, growth of all cells for a few generations without selection, and finally completion of growth under the restrictive and/or selective conditions. This procedure is preferably followed by the density-centrifugation separation of mutant from wild-type cells. Nutritional cross-feeding of procaryotic or eucaryotic mutants by wild-type cells is not a problem. To the contrary, the mutant and wild-type clones are physically separated from each other by the microcapsule membrane as are colonies on agar. More importantly, because the selective phase typically lasts about five to seven generations using microcapsules, any microcapsule colony cross-feeding problems are reduced compared with conventional colonies experiencing longer incubations.

In still yet another embodiment, other substances may be included along with the microorganism during the microencapsulation step. For instance, it may be desirable to include growth hormones such as fibroblast growth factor and/or epidermal growth factor, other non-diffusible growth factors (typically proteins or glycoproteins) or adhesion surfaces, such as fibrinogen, collagen, etc.

For example, adhesion surfaces (or substratum), such as microcarrier beads, may be encapsulated together with the microorganisms. Certain cells require an adhesion surface for growth. The encapsulation of microcarrier beads as the substratum, each bead carrying a single cell, prevents cross-contamination of microorganisms which would otherwise occur between non-encapsulated carrier beads. The encapsulation of microorganisms on beads is particularly useful in growing microorganisms such as normal and malignant mammalian cells which often require the presence of solid substratums. For example, in screening potential anti-cancer drugs, such microencapsulation allows one to follow the inhibition of growth and development of individual cancer cells in the presence of chosen drug regimens.

The present invention also provides the means for solving other prior art problems. For example, conventional agar methods of selecting mutations conferring positive growth advantage have been previously mentioned. When, however, the parental cells exhibit "leaky" growth or grow at a rate just 10–20% slower than the desired mutant, the selection may become problematic. In such a case repeated serial "passage" of a culture may be attempted to enrich for the faster growing mutant. However, if positive selection is performed in microcapsules and in accord with the present invention, the following would be expected. A 200 um diameter microcapsule ($4\times10^{-6}$ ml volume) is formed containing one mutant cell. This cell is a bacterium which in normal medium grows to a cell density of $10^{10}$ cells/ml or about $4\times10^4$ cells/microcapsule. This represents 15 cell doubling (generations). If the mutant's growth is only 10% faster than the parent, then after 14 generations, the "mutant" microcapsules will contain twice as many cells as the other microcapsules. This can provide a sufficient basis for physical separation. The same mutant cells grown by serial passage selection for the same number of generations would simply be enriched two-fold within the bulk parental population. Using calculations, one can rapidly estimate the ability to isolate mutants of other microorganisms given a modest growth rate differential. Thus, the advantages of the present invention are readily apparent.

The present invention also provides a kit for practicing the methods described above. The kit comprises the ingredients or components required to form microcapsules on a laboratory or research scale to screen for mutants in accord with the present invention. As such, the kit comprises a container or package having quality-controlled reagents therein: sterile alginate solution, sterile 2-(cyclohexylamino)ethane sulfonic acid, sterile solution of polylysine having a predetermined molecular weight and a sterile solution of polyethylenimine (PEI) having a predetermined molecular weight. The molecular weights of the polylysine and PEI are predetermined to produce microcapsules having a desired permeability in accord with the known technology as described in, for instance, U.S. Pat. No. 4,352,883. In addition, sterile CaCl$_2$ and mechanical devices for forming microdroplets can be supplied as part of the kit. Preferably, the solutions are provided in sealed sterile vials having sufficient quantities for one experiment. Further, it is preferred that the solutions comprise physiological saline and the polylysine and PEI solutions also contain 0.2M MOPS [3-(N-morpholino)propanesulfonic acid] buffer (pH6).

From the foregoing it will be apparent that isolation of mutant microorganisms in accordance with the present invention can be practiced on a wide variety of organisms, using: (1) a wide variety of techniques to induce the difference in number of microorganisms per capsule between mutant and non mutant-containing microcapsules, and (2) a wide variety of separation techniques to isolate the desired mutant without departing from the scope and spirit of the invention.

It is appreciated that those skilled in the art, upon consideration of this disclosure, may make modifications and improvements within the spirit and scope of this invention.

What is claimed is:

1. A method for isolating a mutant microorganism, which method comprises the steps of:
   a. separately microencapsulating in a semi-permeable membrane each or a small number of microorganisms from a microorganism population containing said mutant;
   b. growing said microencapsulated microorganisms and treating them to induce a difference in cell number between microcapsules containing mutant microorganisms and those containing non-mutant microorganisms; and
   c. separating said microcapsules containing mutant micoorganisms from those containing non-mutant microorganisms by a method based on said difference in cell numbers.

2. The method of claim 1, wherein said mutant microorganism is a naturally occuring mutant of a wild type microorganism.

3. The method of claim 1, wherein the mutation in the mutant microorgahism is artificially induced.

4. The method of claim 3, wherein said artificially-induced mutant is the result of genetic engineering by a biological, biochemical or biophysical process.

5. The method of claim 1, wherein said microcapsules containing said single microorganisms are formed by:
   a. forming a dilute suspension of said microorganisms in a liquid diluent capable of forming a gel upon said dilute suspension having a dilution selected so that there is a high probability that each microcapsule produced from said suspension contains one microorganism;
   b. converting said suspension into gel droplets, forming said microcapsules.

6. The method of claim 1, wherein said treatment comprises growing said microencapsulated microorganisms under conditions restrictive to said mutant whereby said microcapsules containing said mutants have fewer microorganisms per microcapsule than microcapsules containing non-mutants.

7. In the method of claim 6, prior to said separation step, incubating said microcapsules in a high-density medium of appropriate diffusion rate, thereby causing the mutants in the microcapsules which have fewer microorganisms to have a higher density than the non-mutants in the microcapsules which have larger numbers of microorganisms.

8. The method of claim 1 wherein in said growing step (b) the microencasulated mutants have a capacity to accumulate a particular material resulting in an increase in mass and number greater than that of said microencapsulated non-mutants.

9. The method of claim 1, wherein said separation is based on the difference in mass between said microcapsules containing mutant and non-mutant microorganisms and comprises (a) equilibrium density centrifugation of a suspension containing said microcapsules or (b) velocity sedimentation of a suspension containing said microcapsules.

10. The method of claim 1, wherein said microorganisms comprise eucaryotic cells.

11. The method of claim 1, wherein said microorganisms comprise procaryotic cells.

12. The method of claim 1, wherein said microorganisms comprise viruses.

13. The method of claim 1, wherein said microorganisms comprise hybridoma cells.

14. The method of claim 1, wherein mutant microorganisms are selected from chemically complex and non-sterile agricultural, industrial or other commercial process environments.

15. The method of claim 1, wherein said microencapsulated microorganisms are grown in a laboratory culturing medium.

16. The method of claim 1, wherein said microencapsulated microorganisms are grown in an agricultural or industrial process medium wherein one or more species of said microorganism are found in the native environment.

* * * * *